United States Patent
Matthiessen

[11] Patent Number: 5,948,962
[45] Date of Patent: Sep. 7, 1999

[54] GAS DETECTION SYSTEM WITH INTERCHANGEABLE GAS SENSORS

[75] Inventor: Hans Matthiessen, Bad Schwartau, Germany

[73] Assignee: Drägerwerk AG, Lübeck, Germany

[21] Appl. No.: 09/008,846

[22] Filed: Jan. 20, 1998

[30] Foreign Application Priority Data

Jul. 29, 1997 [DE] Germany ............ 197 32 546

[51] Int. Cl.⁶ .................................................. G01N 27/00
[52] U.S. Cl. ........................... 73/23.2; 73/23.3; 73/1.02; 340/632
[58] Field of Search ................... 73/23.2, 23.3, 73/31.05, 1.01, 1.02; 340/632

[56] References Cited

U.S. PATENT DOCUMENTS

| | | | |
|---|---|---|---|
| 4,329,870 | 5/1982 | Farmer | 73/23.2 |
| 4,704,607 | 11/1987 | Teather et al. | 73/1.07 X |
| 4,764,879 | 8/1988 | Campbell . | |
| 5,025,653 | 6/1991 | Schuldt | 73/23.2 |

FOREIGN PATENT DOCUMENTS

| | | |
|---|---|---|
| 38 19 128 | 10/1995 | Germany . |
| 2 284 059 | 5/1995 | United Kingdom . |
| 02783 | 2/1992 | WIPO . |

*Primary Examiner*—Daniel S. Larkin
*Attorney, Agent, or Firm*—McGlew and Tuttle, P.C.

[57] ABSTRACT

A codable gas detection system with at least one interchangeable gas sensor (2), which has standardized plug-type connections (5,6) between the gas sensor (2) and the measuring device (1), but is also able to prevent measured values of an unauthorized gas sensor (2) from being processed. Each gas sensor (2) contains a memory (3) with gas sensor-specific data and is connected via a line to the measuring device (1) with a first calculating and evaluating unit (7), to a downstream memory (8) and preferably to an alarm device (10). Via the second plug-type connection (5), the sensor element (4) proper is connected to a contacting unit (9) in the measuring device (1), and the contacting unit (9) is connected to the first calculating and evaluating unit (7), on the one hand, and to a downstream, second calculating and evaluating unit (11) for the measured value evaluation proper, on the other hand. Measured values from the gas sensor (2) are taken over only if the gas sensor-specific data are accepted by the calculating and evaluating unit (7).

8 Claims, 1 Drawing Sheet

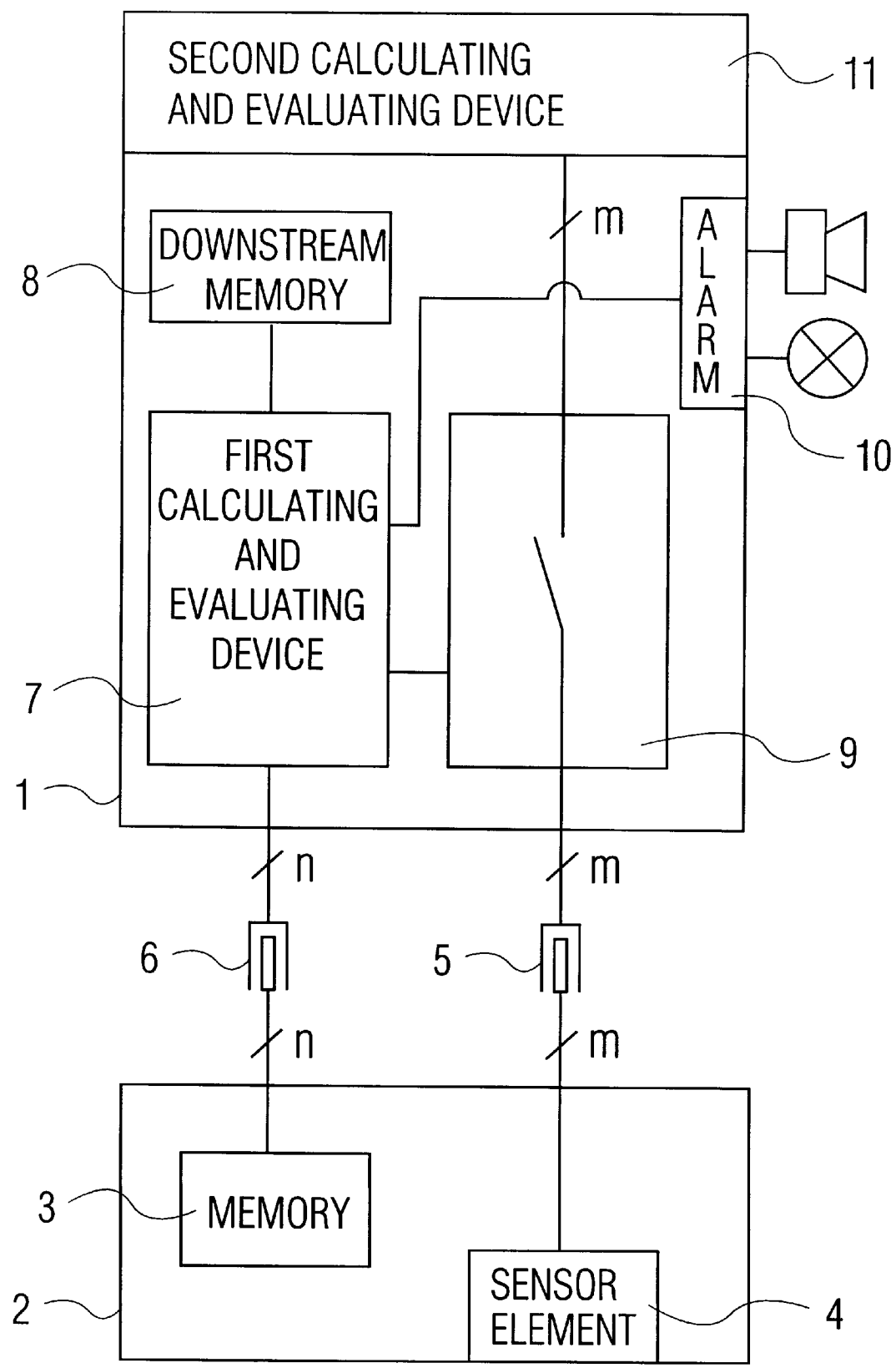

GAS DETECTION SYSTEM WITH INTERCHANGEABLE GAS SENSORS

FIELD OF THE INVENTION

The present invention pertains to a gas detection system with a measuring device which has a mount for at least one interchangeable gas sensor, with a memory, which is located in the measuring device and contains gas sensor-specific data, and with a calculating and evaluating unit.

BACKGROUND OF THE INVENTION

A gas detection system, which comprises a central unit and a plurality of measuring devices on the site, which are connected to the central unit, has been known from DE 38 19 128 C2. Various types of measuring devices may be interchangeably inserted into the measuring devices, and the gas sensors are provided in the base area with an identification system in the form of soldered contact bridges in order for the measuring device to recognize the gas sensor that has been inserted. The prior-art identification system requires a plug in the connection area between the measuring device and the gas sensor with a plurality of plug-type contacts in order to transmit the sensor information in the binary coded form to the measuring device. Such multiple-contact plugs are expensive, on the one hand, and, on the other hand, the fault liability or fault susceptibility increases with increasing number of plug-type contacts. In addition, there is only a limited possibility of retrofitting existing measuring devices for new sensor applications, because the originally designed plug coding must be retained for reasons of compatibility.

SUMMARY AND OBJECTS OF THE INVENTION

The primary object of the present invention is to provide a codable gas detection system with gas sensors, which operates via standardized plug-type connections between the gas sensors and the measuring device, but which is also able to prevent the measured values of unaccepted gas sensors from being processed. This requirement is justified for economical reasons as well as for reasons of product liability.

According to the invention, a gas detection system with a measuring device is provided with a mount for at least one interchangeable gas sensor, with a memory, which is located in the measuring device and contains gas sensor-specific data, and with a calculating and evaluating unit. Each gas sensor also has a memory with gas sensor specific data. This memory is connected to the measuring device via a first plug-type connection and to a downstream memory via a first calculating and evaluating unit contained in the measuring device. This memory is also connected to a contacting unit in the measuring device via a second plug-type connection. The contacting unit is connected to the first calculating and evaluating unit, on the one hand, and to a downstream second calculating and evaluating unit for processing the measured values. With this arrangement, the contacting unit is blocked by the first calculating and evaluating unit only when the latter does not accept each gas sensor accommodated based on the comparison of the gas sensor-specific data read from the memory of each gas sensor with the gas sensor-specific data contained in the downstream memory of the said measuring device.

The memories are, preferably, digital memories and the first calculating and evaluating unit processes digital data.

The plug-type connections between each gas sensor and the receiving measuring device are, preferably, physically arranged in a connection unit.

The second calculating and evaluating unit for processing the measured values of at least one said gas sensor is, preferably, electrically connected to each gas sensor by means of a plug-type connection and/or receives the measured values in a wireless manner, preferably in the form of infrared signals. The memory of the measuring device takes over the gas sensor-specific data of each gas sensor mounted newly for the first time from the memory of the gas sensor and stores them.

The gas sensor, of which there is at least one, is, preferably, an electrochemical ethanol sensor, and the second calculating and evaluating unit sends a release signal for starting the engine of a motor vehicle only if the gas sensor is accepted by the first calculating and evaluating unit, based on the comparison of the gas sensor-specific data read from the memory of the gas sensor with the gas sensor-specific data contained in the memory of the measuring device.

Alternatively,
a) either the contacting unit is contacted through when it is determined by the comparison of the data that the gas sensor-specific data contained in the memory of each gas sensor agree with the corresponding data in the memory of the measuring device, or
b) the contacting unit is blocked if it is determined by the comparison of the data that the gas sensor-specific data contained in the memory of each gas sensor do not agree with the corresponding data in the memory of the measuring device.

The advantage of the present invention is mainly the fact that the gas sensor-specific data stored in a memory of the gas sensor either lead to a blocking of the measurement proper, preferably combined with the triggering of an alarm by an alarm device with optical and/or acoustic signaling, in the case of nonacceptance after evaluation in the measuring device, or they make possible a normal measurement in the case of acceptance. An effective possibility of preventing the use of gas sensors not authorized by the manufacturer or operator of the measuring device is thus disclosed.

A normal measurement with corresponding evaluation in the measuring device takes place only in the case of agreement of the, preferably coded data specific of the particular gas sensor with the corresponding data in the memory of the measuring device, i.e., in the case of acceptance, and the measured data line is or remains otherwise blocked and an alarm may be additionally triggered. The terms "measuring head" and "gas sensor" known for gas measurement are used in this application for simplicity's sake, but it would also be possible to use the more general term "measuring device" instead of "measuring head" as well as the more general term "sensor" instead of "gas sensor."

The subject of the present invention is, in the general sense, assembly units that are connected to one another via electronic connections and assume a function together. For example, a sensor, which is connected to a measuring device via a plug-type connection, assumes a measuring function with the measuring device.

To standardize the plug-type connections for measuring devices of the same type, the same type of plug-type connection is, preferably, used. However, this has the drawback that other sensors from other manufacturers or suppliers also fit the socket of the measuring device and may generate false measured values or even cause damage to sensors or the measuring device if they are electrically incompatible.

The solutions suggested in the past, according to which mechanical coding is provided on the plug-type connections, have proved to be impractical, expensive and frequently of poor stability.

Another drawback is that a relatively small number of possible codings must be used, so that identical plugs are again ultimately used for different sensors.

The design and the mode of operation of the present invention is explained by means of the only figure based on an exemplary embodiment from the field of gas measurement.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawings:

The only FIGURE is a schematic view of a system according to the invention.

DESCRIPTION OF THE PREFERRED EMBODIMENTS

Referring to the drawings in particular, the gas detection system according to the present invention comprises essentially a measuring head or measuring device 1 and at least one gas sensor 2. The gas sensor 2 is electrically connected to the measuring device 1 via detachable plug-type connections 5, 6. The gas sensor 2 contains a memory 3 with sensor-specific data, which is connected by a corresponding line to the measuring device 1 via the plug-type connection 6, as well as the measuring element proper, i.e., the sensor element 4. In the case of an electrochemical gas sensor, this would be an electrochemical measuring cell. The sensor element 4 is connected to the measuring device 1 via a second plug-type connection 5 and a line that is electrically parallel to the first one. In an alternative embodiment the second connection conveys measured values in a wireless manner preferably in the form of infrared signals. The measuring device 1 contains a first calculating and evaluating unit 7 with a downstream memory 8. The calculating and evaluating unit 7 and the memory 8 may also be designed as a single (micro)electronic component. On the other hand, the calculating and evaluating unit 7 is in connection with a contacting unit 9 and preferably an alarm device 10 with acoustic and/or optical indication or signal transmitters. A second calculating and evaluating unit 11, which is used for the processing proper of the measured values arriving from the gas sensor 2, is connected to the contacting unit 9.

The mode of operation of the gas detection system described is as follows: After plugging the gas sensor 2 into the socket of the measuring device 1 with the plug-type connections 5, 6, the memory 3 of the gas sensor 2 is first read by the first calculating and evaluating unit 7. The data record contains gas sensor-specific data, especially in the coded form. By comparing these sensor data with the data contained in the memory 8 of the measuring device 1, the calculating and evaluating unit 7 determines whether the gas sensor 2 plugged in is permissible, i.e., authorized for the measurement proper. If yes, the contacting unit 9, which was blocked until then, is released or contacted, so that the measured signals proper can enter the measuring device 1 or the second calculating and evaluating unit 11 from the sensor element 4 in the gas sensor 2 via the line with the plug-type connection 5.

If the gas sensor 2 is unacceptable, an activating signal is sent by the calculating and evaluating unit 7 to the alarm device 10, and the contacting unit is or remains blocked until a permissible gas sensor 2 is identified.

The present invention may be used especially advantageously in the field of stationary gas-measuring technique, where modern measuring devices for gas-measuring units take over a characteristic data record necessary for recognizing the sensor from the sensor plugged in first in the case of installation and then accept only sensors provided with the same characteristic data.

Another example of a preferred use of the present invention is a control or blocking device for a motor vehicle, which is based on the driver's breath alcohol measurement. The corresponding, interchangeable ethanol sensor also contains a coded, sensor-specific data record, so that the corresponding measuring and switching unit can determine whether the sensor is authorized for the measurement. The corresponding electric signals and the desired release functions for the breath alcohol measurement and optionally for the subsequent ignition of the engine of the motor vehicles are correspondingly passed on in a positive case. In the negative case, i.e., in the case of the use of an unauthorized sensor, the subsequent functions are blocked and ignition of the engine is no longer possible, at any rate not in connection with a preceding authorized ethanol measurement.

While specific embodiments of the invention have been shown and described in detail to illustrate the application of the principles of the invention, it will be understood that the invention may be embodied otherwise without departing from such principles.

What is claimed is:

1. A detection system, comprising:
   at least one interchangeable sensor;
   a measuring device with a mount for said at least one interchangeable sensor;
   a downstream memory located in said measuring device which contains sensor-specific data;
   a first calculating and evaluating unit in said measuring device;
   a sensor memory with sensor-specific data associated with each said at least one interchangeable sensor;
   a first plug-type connection connecting said at least one interchangeable sensor to said measuring device and to said downstream memory via said first calculating and evaluating unit;
   a contacting unit in said measuring device;
   a second calculating and evaluating unit for processing measured values;
   a second plug-type connection connecting said at least one interchangeable sensor to said contacting unit, said contacting unit being connected to said first calculating and evaluating unit and to said second calculating and evaluating unit for processing measured values, so that said contacting unit is blocked by said first calculating and evaluating unit only when said first calculating and evaluating unit does not accept each sensor accommodated based on a comparison of said sensor-specific data read from the said sensor memory with sensor-specific data contained in said downstream memory of said measuring device.

2. The detection system in accordance with claim 1, wherein said sensor memory and said downstream memory are digital memories and said first calculating and evaluating unit is a digital processing unit which processes digital data.

3. The detection system in accordance with claim 1, wherein said plug-type connections between each said sensor and said measuring device are physically arranged in a connection unit.

4. The detection system in accordance with claim 1, wherein said second calculating and evaluating unit is for processing measured values of said at least one interchangeable sensor and is electrically connected to each said at least one interchangeable sensor by means of said second plug-type connection and/or receives measured values in a wireless manner, preferably in a form of infrared signals.

5. The detection system in accordance with claim 1, wherein said memory of said measuring device takes over sensor-specific data of each additional at least one interchangeable sensor newly mounted in said measuring device for the first time from said sensor memory of said at least one interchangeable sensor and stores them.

6. The detection system in accordance with claim 1, wherein said at least one interchangeable sensor is an electrochemical ethanol sensor, and said second calculating and evaluating unit sends a release signal for starting an associated engine of a motor vehicle only if said sensor is accepted by said first calculating and evaluating unit based on said comparison of the sensor-specific data read from said memory of the said sensor with said sensor-specific data contained in said downstream memory of said measuring device.

7. The detection system in accordance with claim 1, wherein alternatively, either:

a) said contacting unit is contacted when it is determined by said comparison of the data that the sensor-specific data contained in said memory of each said sensor agree with the corresponding data in said downstream memory of said measuring device; or b) said contacting unit is blocked if it is determined by the comparison of data that said sensor-specific data contained in said memory of each said sensor do not agree with the corresponding data in said memory of said measuring device.

8. A gas detection process, comprising:

providing at least one interchangeable gas sensor;

providing a measuring device with a mount;

mounting said at least one interchangeable gas sensor to said measuring device;

providing a downstream memory located in said measuring device which contains gas sensor-specific data;

providing a first calculating and evaluating unit in said measuring device;

providing a gas sensor memory with gas sensor-specific data associated with each said at least one interchangeable gas sensor;

providing a first plug-type connection connecting said at least one interchangeable gas sensor to said measuring device and to said downstream memory via said first calculating and evaluating unit;

providing a contacting unit in said measuring device;

providing a second calculating and evaluating unit for processing measured values;

providing a second plug-type connection connecting said at least one interchangeable gas sensor to said contacting unit;

connecting said contacting unit to said first calculating and evaluating unit and to said second calculating and evaluating unit;

processing measured values, so that said contacting unit is blocked by said first calculating and evaluating unit only when said first calculating and evaluating unit does not accept each gas sensor accommodated based on a comparison of said gas sensor-specific data read from the said gas sensor memory with gas sensor-specific data contained in said downstream memory of said measuring device.

* * * * *